United States Patent
Hilding et al.

(10) Patent No.: US 10,667,054 B2
(45) Date of Patent: May 26, 2020

(54) ACOUSTIC HEADSET WITH INTEGRATED TWO-WAY DIGITAL AND ANALOG COMMUNICATION COMPONENTS

(71) Applicant: 3M INNOVATIVE PROPERTIES COMPANY, St. Paul, MN (US)

(72) Inventors: Karl S. I. Hilding, Värnamo (SE); Marcus J. Ekblad, Värnamo (SE); Petter M. Igede, Värnamo (SE)

(73) Assignee: 3M Innovative Properties Company, St. Paul, MN (US)

( * ) Notice: Subject to any disclaimer, the term of this patent is extended or adjusted under 35 U.S.C. 154(b) by 64 days.

(21) Appl. No.: 16/302,708

(22) PCT Filed: May 16, 2017

(86) PCT No.: PCT/US2017/032806
§ 371 (c)(1),
(2) Date: Mar. 12, 2019

(87) PCT Pub. No.: WO2017/205107
PCT Pub. Date: Nov. 30, 2017

(65) Prior Publication Data
US 2019/0200125 A1  Jun. 27, 2019

Related U.S. Application Data

(60) Provisional application No. 62/341,782, filed on May 26, 2016.

(51) Int. Cl.
*H04R 5/033* (2006.01)
*H04R 3/00* (2006.01)
(Continued)

(52) U.S. Cl.
CPC ............... *H04R 3/04* (2013.01); *A61F 11/14* (2013.01); *G10L 21/0232* (2013.01);
(Continued)

(58) Field of Classification Search
CPC .......... H04R 5/033; H04R 5/02; H04R 3/007; H04R 2420/03; H04R 2225/61;
(Continued)

(56) References Cited

U.S. PATENT DOCUMENTS 5,426,719 A    6/1995  Franks
8,190,438 B1 *  5/2012  Nelissen ................. G10L 21/00
                                                          381/85

(Continued)

FOREIGN PATENT DOCUMENTS

CA          129247      9/2009
CN        105225662  *  1/2016  ............. G10L 15/26
(Continued)

OTHER PUBLICATIONS

"2-Way Communication Ear Muffs (built in radio)—Electronic Ear Muff", Earplug Superstore, May 22, 2016, [Retrieved from the internet on Jun. 30, 2017], URL <https://web.archive.org/web/20160522111049/http://www.earplugstore.com/electromc-industnal-ear-muffs.html>, 3 pages, XP055386758.
(Continued)

*Primary Examiner* — Vivian C Chin
*Assistant Examiner* — Ubachukwu A Odunukwe
(74) *Attorney, Agent, or Firm* — Katherine M. Scholz; Dena M. Ehrich (57) ABSTRACT

In some examples, an acoustic headset for providing hearing protection, includes: a first auditory cup; a second auditory cup; at least one of a stirrup or headband interconnecting the first and second auditory cups; at least one speaker integrated within at least one of the first auditory cup or the second auditory cup; a microphone that receives sound, wherein the microphone is coupled to the acoustic headset; and wherein at least one of the first and second auditory cups comprises a digital component for transmission and receipt
(Continued)

of digital wireless audio communications, and wherein at least one of the first and second auditory cups comprises an analog component for transmission and receipt of analog wireless audio communications.

18 Claims, 10 Drawing Sheets

(51) Int. Cl.
*H04S 7/00* (2006.01)
*G10L 25/78* (2013.01)
*A61F 11/06* (2006.01)
*H04R 3/04* (2006.01)
*H04R 5/04* (2006.01)
*H04R 1/10* (2006.01)
*A61F 11/14* (2006.01)
*G10L 21/0232* (2013.01)

(52) U.S. Cl.
CPC .......... *H04R 1/1083* (2013.01); *H04R 5/033* (2013.01); *H04R 5/04* (2013.01); *H04R 1/1008* (2013.01); *H04R 2420/07* (2013.01); *H04R 2460/01* (2013.01)

(58) Field of Classification Search
CPC ....... H04R 1/1083; H04S 7/308; A61F 11/14; A61F 11/06; A61F 11/08; G10L 21/00; G10L 25/78; H04B 5/00
USPC ......... 381/74, 310, 55, 58, 59, 85; 455/3.05, 455/435.3, 526, 140, 166.2
See application file for complete search history.

(56) References Cited

U.S. PATENT DOCUMENTS

| | | |
|---|---|---|
| 1,005,135 A1 | 8/2018 | Liu |
| 2006/0147052 A1 | 7/2006 | Wikel |
| 2007/0165875 A1 | 7/2007 | Rezvani |
| 2007/0258608 A1 | 11/2007 | Neihoff |
| 2010/0119077 A1* | 5/2010 | Platz ...................... A61F 11/08 381/72 |
| 2010/0215170 A1 | 8/2010 | Kannanppan |
| 2011/0317844 A1 | 12/2011 | Schreuder |
| 2014/0254842 A1 | 9/2014 | Smith |
| 2014/0363004 A1 | 12/2014 | Porjo |
| 2015/0055784 A1 | 2/2015 | Brayton |
| 2015/0365760 A1 | 12/2015 | Jiang |
| 2016/0021450 A1 | 1/2016 | Kulavik |
| 2016/0050474 A1 | 2/2016 | Rye |
| 2016/0085305 A1 | 3/2016 | Spio |

FOREIGN PATENT DOCUMENTS

| | | |
|---|---|---|
| EP | 1828833 | 8/2015 |
| TW | 201014578 | 4/2010 |
| WO | 2014/177909 | 11/2014 |

OTHER PUBLICATIONS

"Sensear Smart Muff Dual Protection Headband Model SMSDPSRI With SENS(TM) Face-To-Face + Two-Way Radio + BlueTooth + Short Range Communications (NRR 30)—BlueTooth Compatible Communications Headsets", Earplug Superstore, May 17, 2016, [Retrieved from the internet on Jun. 30, 2017], URL <https://web.archive.org/web/20160517172320/http://www.earplugstore.com:80/sensear-smsdpsrl.html>, 2 pages, XP055386765.
International Search Report for PCT International Application No. PCT/US2017/032806, dated Jul. 10, 2017, 5 pages.

* cited by examiner

ACOUSTIC HEADSET WITH INTEGRATED TWO-WAY DIGITAL AND ANALOG COMMUNICATION COMPONENTS

Cross Reference to Related Applications

This application is a national stage filing under 35 U.S.C. 371 of PCT/US2017/032806, filed May 16, 2017, which claims the benefit of U.S. Provisional Application No. 62/341,782, filed May 26, 2016, the disclosure of which is incorporated by reference in its/their entirety herein.

TECHNICAL FIELD

The present application relates generally to acoustic headsets, and more specifically, to providing communication within an acoustic headset.

BACKGROUND

Noisy environments, such as worksites, airfields, and the like, may include noise sources that have the potential to damage the hearing of a person. A person operating in a noisy environment may experience hearing loss from acute acoustic trauma or gradually developing noise-induced hearing loss. Acute acoustic trauma may cause hearing loss from a one-time exposure to an excessive noise level, whereas gradually developing noise-induced hearing loss may result from exposure to unsafe noise levels over an extended period of time.

To prevent hearing damage, a person operating in noisy environment may wear hearing protection. Hearing protection may be passive or active. Passive hearing protection includes earplugs and earmuffs that block noise up to a particular noise level. Active hearing protection may include earmuffs that permit certain types of noise to pass through to a person by electronically filtering out particular decibels or frequencies.

Although various forms of hearing protection may provide adequate protection against excessive noise, persons wearing such hearing protection may need to communicate with one another. In noisy environments, communicating with one another may be difficult while wearing hearing protection due to noise from noise sources and filtering from the hearing protection. In some scenarios, a person wearing hearing protection may carry an additional and separate communication device to facilitate communication with other individuals in a noisy environment. Although separate communication devices may facilitate such communication, the person may be required to carry two separate devices (hearing protection and communication device), which may be coupled by a cable. Such two-device configurations can impede a person's movement, hinder the likelihood of communicating, and/or potentially introduce safety risks (e.g., if the cable becomes entangled on the user or other objects in the environment).

DETAILED DESCRIPTION

This disclosure is directed to an acoustic headset for providing hearing protection, wherein the acoustic headset includes both digital and analog components for transmission and receipt of digital and analog wireless audio communications. Rather than only including analog components for transmission and receipt of analog wireless audio communications, or only including digital components for transmission and receipt of digital wireless audio communications, the acoustic headset described in this disclosure includes components that enable both digital and analog wireless audio communications to other acoustic headsets or other computing devices. In this way, the disclosed acoustic headset may provide for both digital and analog two-way communications using components that are integrated within auditory cups of the acoustic headset. By miniaturizing the digital and analog components to fit within the auditory cups of the acoustic headset, a user of the acoustic headset may not have to carry additional communications equipment to enable both digital and analog two-way communications. By eliminating the need to carry additional communications equipment, the disclosed acoustic headset may improve the safety of the user by avoiding the need for a wired communication link between a headset and additional communications equipment, which might otherwise become entangled in a work environment. In some instances, by eliminating the need to carry additional communications equipment, the weight of communications equipment carried by the user may be reduced thereby improve the range of motion/movement of the user. As such, in some examples, no additional digital components external to the acoustic headset may be used to assist a digital component of headset 100 in the transmission and receipt of the digital wireless audio communications. In some examples, no additional analog components external to the acoustic headset may be used to assist an analog component of headset 100 in the transmission and receipt of the analog wireless audio communications.

Figure 1:
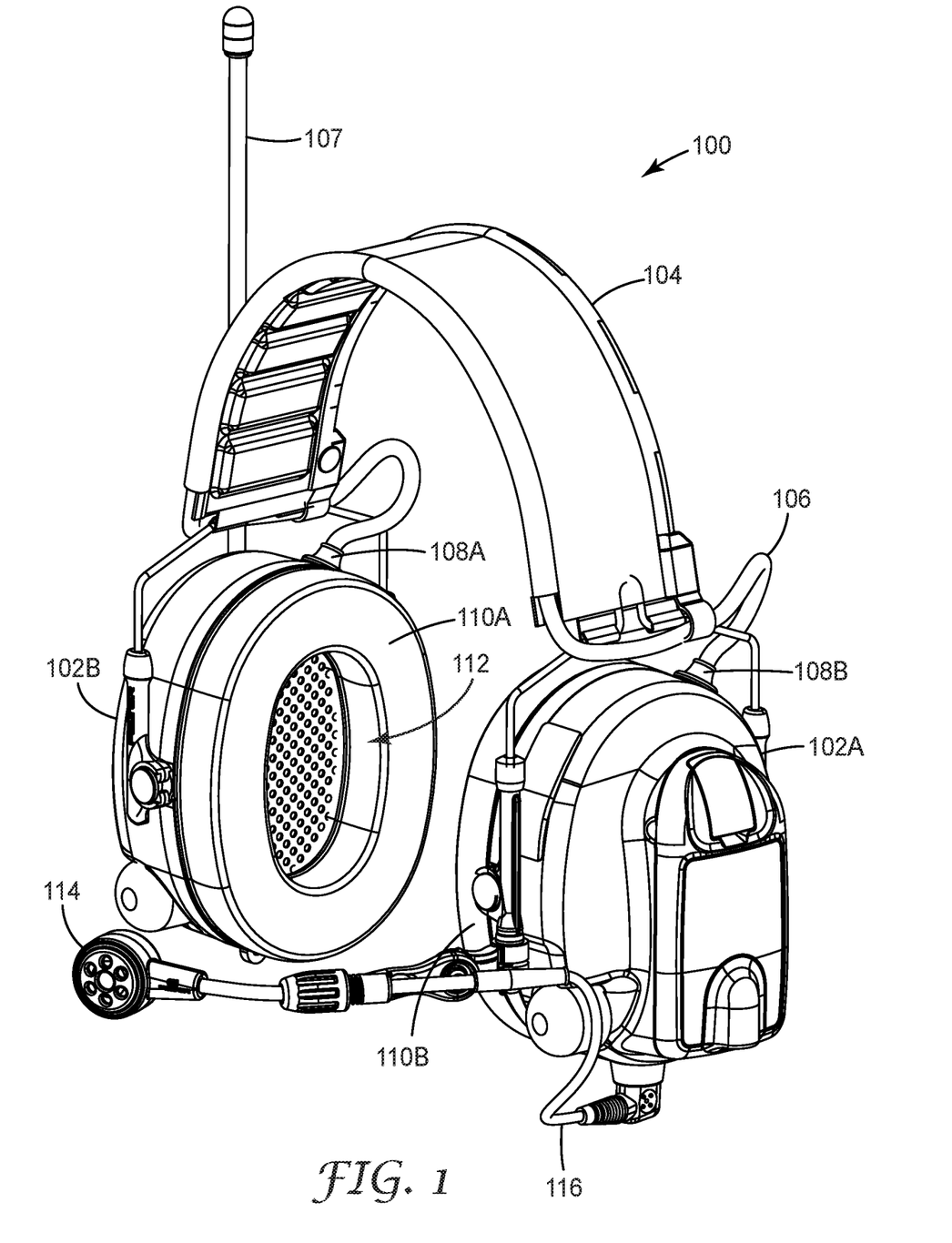
FIG. 1 is a diagram illustrating an example protective headset that includes digital and analog two-way communication components, in accordance with techniques of this disclosure.

FIG. 1 is a diagram illustrating an example protective headset 100 that includes digital and analog two-way communication components, in accordance with techniques of this disclosure. As shown in FIG. 1, protective headset 100 includes first auditory cup 102A and second auditory cup 102B. Auditory cups 102A and 102B are physically coupled by a stirrup or headband 104. Stirrup or headband 104 may be comprised of any rigid or semi-rigid material, such as plastic, aluminum, steel or any other suitable material. Protective headset 100 may include one or more antennas, such as antenna 107 to receive digital and/or analog signals from devices that are remote from protective headset 100. As further described in this disclosure, auditory cups 102A and 102B may include hardware that provides digital and analog two-way communication. Such hardware may be implemented, in part, with printed circuit boards and components integrated in the printed circuit boards.

In examples where the hardware that provides digital and analog two-way communication is distributed between first auditory cup 102A and second auditory cup 102B, such as FIG. 1, one or more communication links may communicatively couple the distributed hardware. For instance, headset 100 includes communication link 106, which communicatively and physically couples hardware auditory cups 102A, 102B that provide digital and analog two-way communication. Examples of communication link 106 may include one or more strands of wire comprised of copper, aluminum, silver or other suitable conducting material. The ends of communication link 106 may enter auditory cups 102A, 102B via ports 108A, 108B, and couple to hardware such as printed circuit boards included within each of auditory cups 102A, 102B.

FIG. 1 illustrates cushions 110A and 110B that are attached or otherwise affixed to auditory cups 102A and 102B. Cushions 110A and 110B may abut around the ears of the wearer of headset 100. Cushions 110A and 110B contribute in the capability of auditory cups 102A, 102B to dampen or otherwise reduce ambient sound from an environment outside of auditory cups 102A, 102B. Cushions 110A and 110B may be comprised of any compressible and/or expanding material, such as foam, gel, air, or any other such suitable material. Auditory cups 102A, 102B may be comprised of any rigid or semi-rigid material, such as a plastic, which in some cases, may be a non-conductive, dielectric plastic.

Auditory cup 102B includes loudspeaker component 112. In some examples, auditory cup 102A may also include a loudspeaker component similar to or the same in structure in functionality as loudspeaker component 112. Loudspeaker component 112 may emit sound based on an analog or digital signal received or generated by headset 100. Loudspeaker component 112 may include one or more electroacoustic transducers that convert electrical audio signals into sound. Some example loudspeaker components may include a magnet, voicecoil, suspension and diaphragm or membrane. Loudspeaker component 112 may be communicatively coupled to the hardware that provides digital and analog two-way communication. As an example, if headset receives a signal representing voice communication, loudspeaker component 112 may emit sound corresponding to the signal.

Headset 100 also includes a microphone 114. Microphone 114 may be communicatively and/or physically coupled to the hardware that provides digital and analog two-way communication is distributed between first auditory cup 102A and second auditory cup 102B, such as FIG. 1. Microphone 114 may be any device that translates sound into electrical audio signals. For instance, a person wearing headset 100 may speak, thereby generating sound that is received by microphone 114. Microphone 114 may convert the spoken sounds into electrical audio signals that are received by the hardware that provides digital and analog two-way communication. Electrical audio signals may be transmitted to hardware that provides digital and analog two-way communication via communication link 116.

Figure 2:
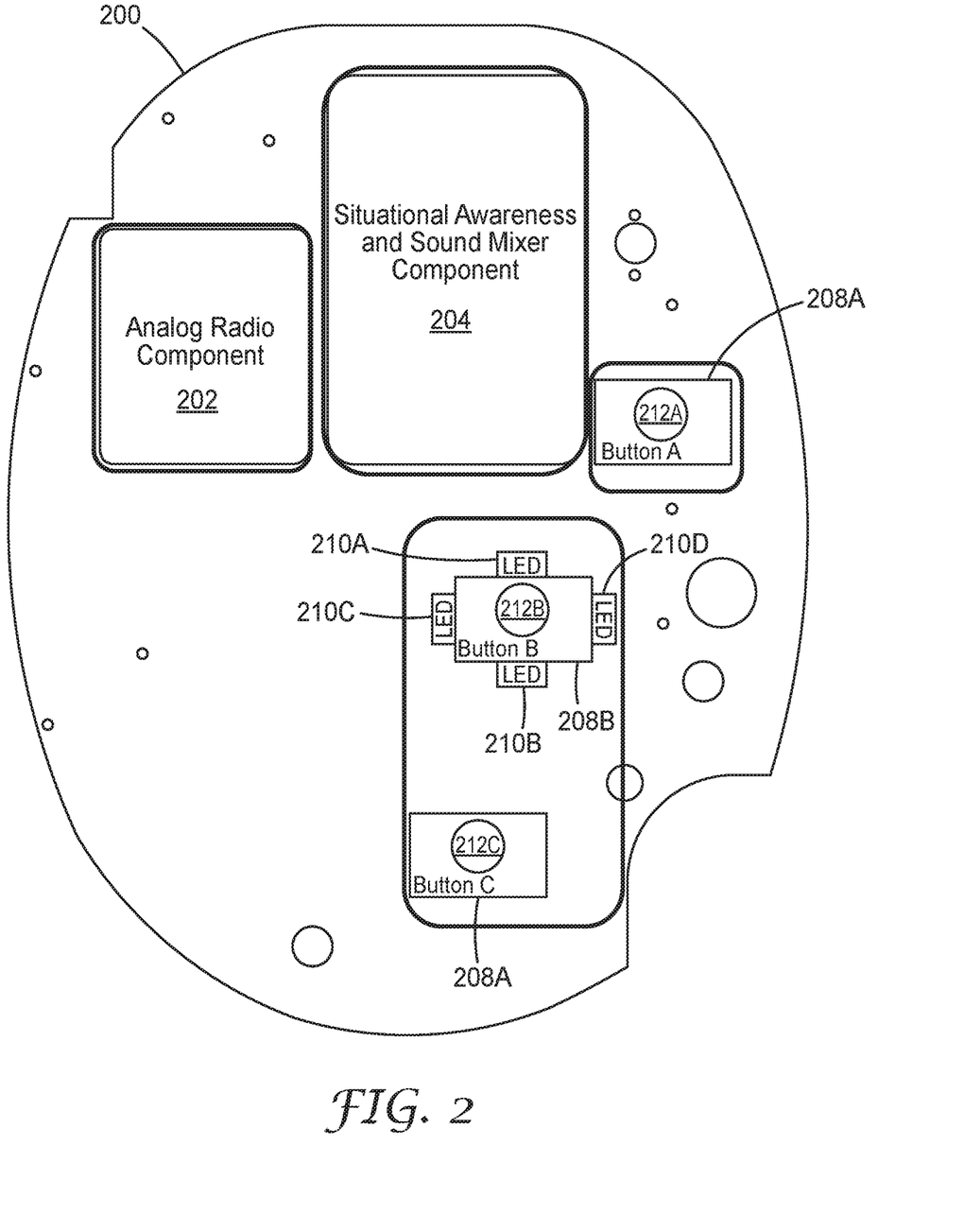
FIG. 2 illustrates a printed circuit board that includes digital and analog two-way communication components, in accordance with techniques of this disclosure.
Figure 3:
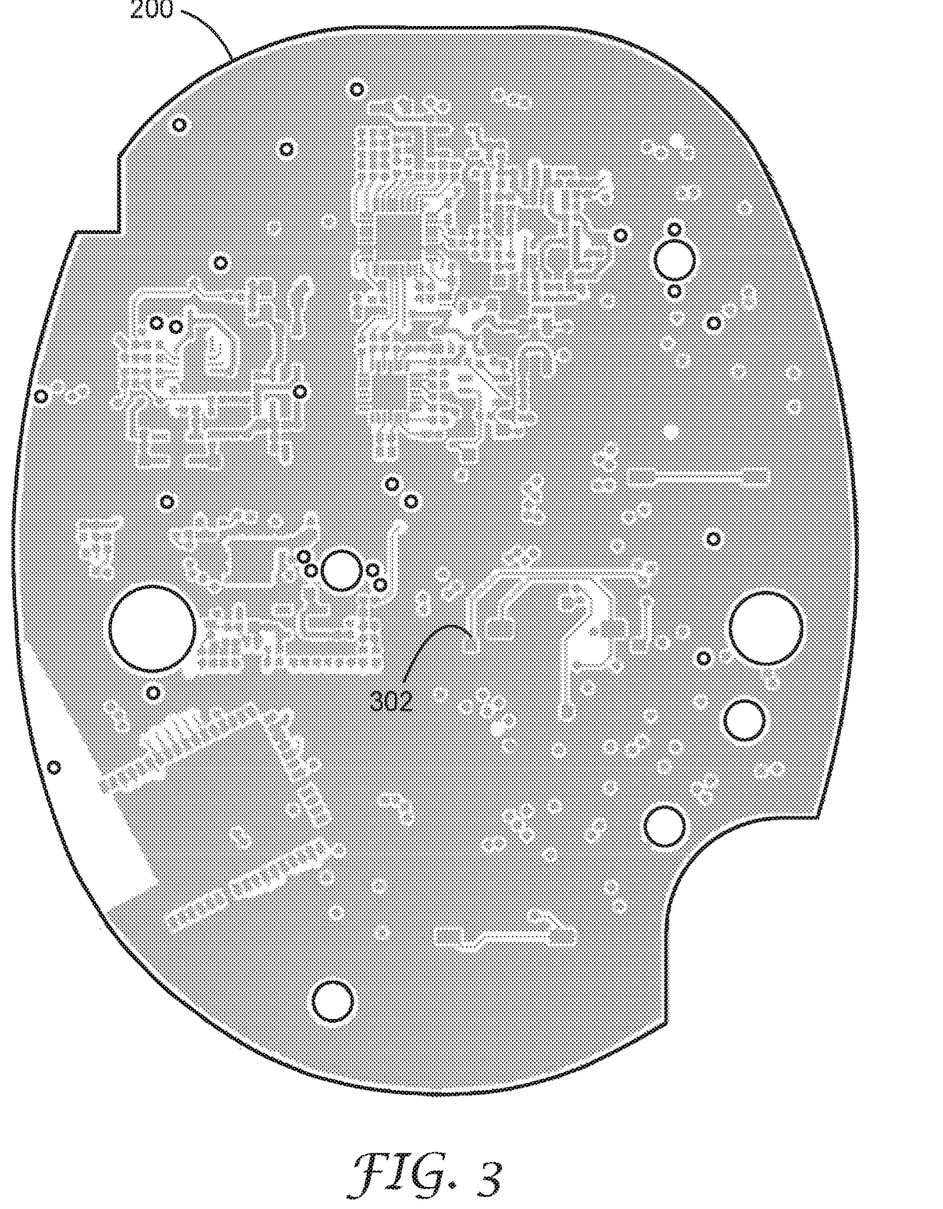
FIG. 3 illustrates traces of the first side of a printed circuit board, in accordance with one or more techniques of the disclosure.

FIG. 2 illustrates a printed circuit board 200 that includes digital and analog two-way communication components, in accordance with techniques of this disclosure. As further shown in FIG. 3, printed circuit board 200 may include a set of traces that communicatively couple electrical components to one another. Printed circuit board 200, as shown in FIG. 2, illustrates a first side of printed circuit board 200. Various components may be attached to printed circuit board 200 including, but not limited to analog radio component 202, situational awareness and sound mixer component 204, wireless communication component 206, switches 208A-208C, and lights 210A-210D. One or more of the components attached to printed circuit board 200 may be communicatively coupled to one or more other components via the traces as further illustrated in FIG. 1. Each of the components identified in FIG. 2 may be further comprised of one or more electrical components as shown in FIG. 3.

Analog radio component 202 controls the frequency on which communications are sent and received wirelessly between headset 100 and one or more other communication devices. As further illustrated in FIG. 5, printed circuit board 200 may include components that provide for digital and analog wireless communication between headset 100 and one or more other communication devices. Analog radio component 202 may be set by a microprocessor (e.g., microprocessor and memory 508) to a specific frequency with which headset 100 sends communications and receives communications. In some examples, the frequency may be set by a user via a user interface. In other examples, the frequency may be set by coupling headset 100, and more specifically a printed circuit board included in headset 100 to another computing device 100 which sends data to the microprocessor indicating the frequency which headset 100 will send and receive wireless communications. An analog built in two way radio is programmable to different frequencies between 403 MHz-470 MHz, in some examples. As long as any other radio has the same frequency programmed it is possible to communicate between each other.

Figure 5:
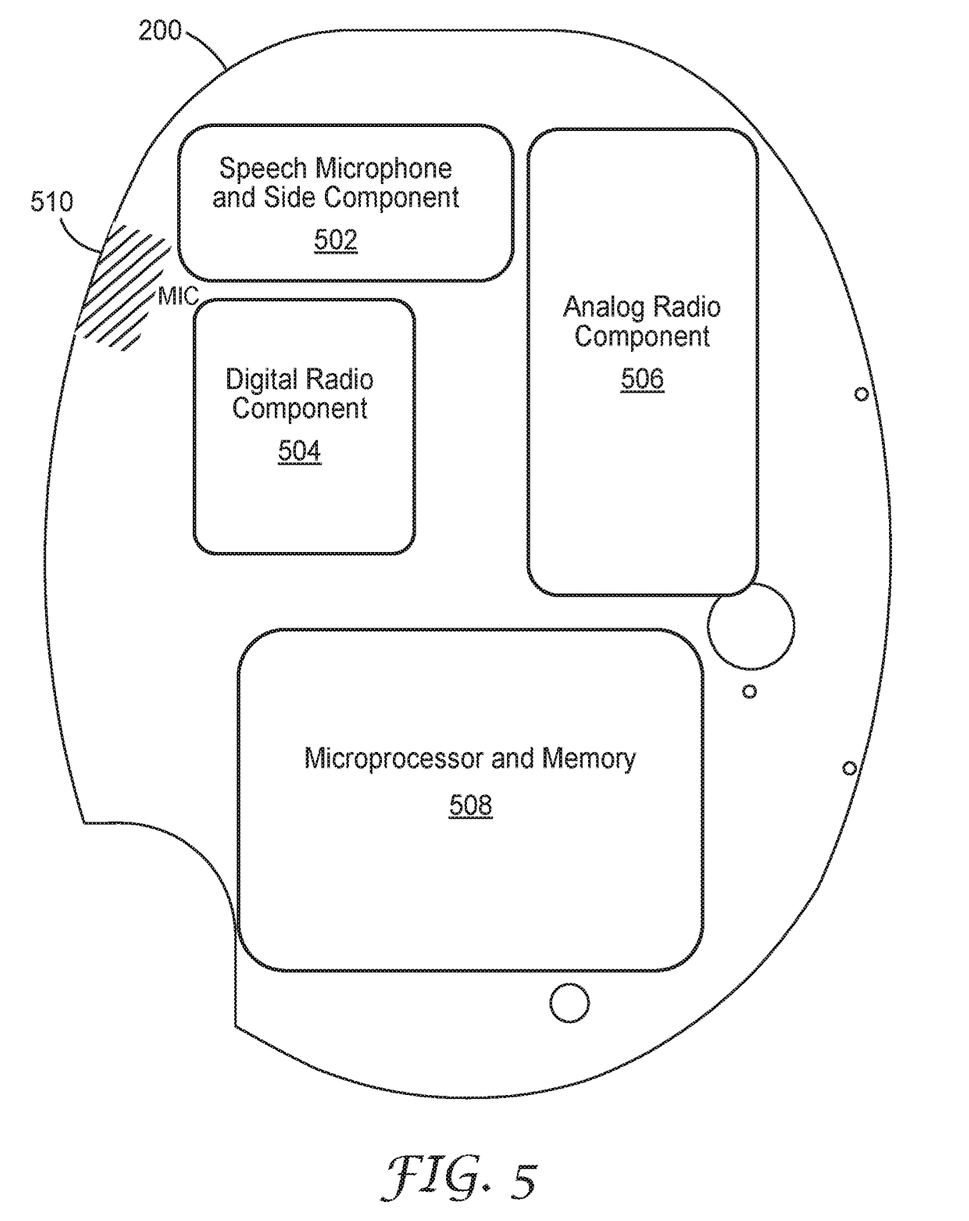
FIG. 5 illustrates sub-components of the various components on a second side of a printed circuit board, in accordance with one or more techniques of the disclosure.

Analog radio component 202 may receive an audio signal from digital radio component 504 or analog radio component 506 as which in FIG. 5. The audio signal may represent audio capture by microphone 114. Analog radio component 202 may transmit the audio signal on the frequency to which analog radio component 202 is set. Analog radio component 202 may also receive an audio signal from another computing device on a frequency to which analog radio component 202 is set. Analog radio component 202 may convert the received audio signal to another signal that is interpretable by one or more components shown in FIG. 5. For instance, one or more of digital radio component 504, analog radio component 506, and/or microprocessor and memory 508 may receive the signal. In this way, analog radio component 202 may receive audio signals on a frequency and send the audio signals to other components of headset 100. Analog radio component 202 may send audio signals received from other components of headset 100 to other computing devices. A digital built in two way radio (e.g., digital radio component 504) is programmable to different frequencies between 403 MHz-470 MHz. As long as any other radio has the same frequency and the correct code programmed it is possible to communicate between each other.

Printed circuit board 200 includes situational awareness and sound mixer component 204 (SASMC 204). SASMC 204 may receive an audio signal from microphone 508, which microprocessor 508 received from microphone 510 and/or microphone 114, as shown in FIGS. 1 and 5 respectively. Microphone 510 may capture ambient audio of an environment in which headset 100 is used, while microphone 114 may capture spoken words of a user of headset 100. SASMC 204 may receive one or more audio signals from microprocessor 508 and cause speakers 112 to output the one or more audio signals. In this way, SASMC 204 may enable a user of headset 100 to hear audio that corresponds to the user's speech and/or environment of headset 100. In some examples SASMC 204 may determine which audio is output to speakers 112. For instance, if headset 100 is outputting audio from another computing device via data receiving using wireless component 206 (e.g., Bluetooth audio from another computing device) and headset 100 receives an incoming audio signal via analog radio component 202, SASMC 204 may receive the audio from microprocessor 508 and output the audio from the analog radio component 202 at speakers 112 thereby interrupting the audio that was output from the other computing device. SASMC 204 may determine which of speakers 112 outputs one or more portions or channels of an audio signal.

As shown in FIG. 2, printed circuit board 200 includes wireless component 206. In some examples, wireless component 206 may provide for wireless communication using any number of protocols such as Bluetooth, WiFi, or any other suitable protocol for transmitting data. In some examples, data received at wireless component 206 from another computing device (e.g., music data from a smartphone) may be sent to microprocessor 508. Microprocessor 508 may send the data to SASMC 204, which causes audio corresponding to the received data to be output at one or more of speakers 112.

Printed circuit board 200 also includes switches 208A, 208B, and 208C. In some examples, switches 208A-208C may be implemented as mechanical button switches that may be pressed by a user, although in other examples any suitable user input hardware may be used that generates a signal when actuated by a user. Although not shown in FIG. 1, each of switches 208A-208C may be mounted within auditory cup 102B or 102A, such that one or more of button surfaces 212A-212C may be pressed or touched by a user thereby causing the respective switches 208A-208C to send respective press signals to microprocessor 508. As further described in this disclosure, based on the particular buttons that are pressed, microprocessor 508 may perform one or more functions. Printed circuit board 200 may also include one or more LEDs 210A-210D. As further described in this disclosure, one or more of LEDs 210A-210D may be turned on (e.g., emit light) or turned off (not emit light) based on signals from microprocessor 508. In some examples one or more of LEDs 210A-210D may be white or non-which in color. For instance, one or more of LEDs 210A-210D may be blue, red, or any other color.

In some examples, printed circuit board 200 may have dimensions of 6.5 cm width×8.3 cm height. In some examples, printed circuit board 200 may be larger or smaller than 6.5 cm width×8.3 cm height. For instance, printed circuit board may have dimensions in a range of 4.5 cm width×6.3 cm height to 8.5 cm width×10.3 cm height. In some examples, printed circuit board 200 may have a surface area of 55 square centimeters or less. In some examples, one or more audio cups of headset 100 may each include dimensions of 4.9 cm depth×10.8 cm height×8.3 cm width. In some examples, the one or more audio cups may each have a cavity. The cavity may include a printed circuit board such as printed circuit board 200. The cavity may have a cubic volume of 425 cubic centimeters or less. In some examples, the dimensions and cubic volume may be larger or smaller. For instance, one or more audio cups of headset 100 may have dimensions in a range of 2.9 cm depth×8.8 cm height×6.3 cm width to 8.9 cm depth×14.8 cm height×12.3 cm width.

In some examples, one or more components of printed circuit board 200 may be distributed to a second circuit board, wherein the second circuit board is included in the other auditory cup of headset 100 that does not include printed circuit board 200. In this way, one or more components may be distributed in the two different auditory cups, wherein the components may be communicatively coupled by a communication link between the respective printed circuit boards that include the respective components.

FIG. 3 illustrates traces of the first side of printed circuit board 200, in accordance with one or more techniques of the disclosure. Example trace 302 may provide an electrically communicative coupling between one or more components or sub-components attached to printed circuit board 200. Traces may be electrically conducting thereby enabling the transmission of electrical signals between components and sub-components. The various components on circuit board 200, illustrated in FIG. 2, may be attached to printed circuit board 200. The various components of circuit board 200 as illustrated in FIG. 2, may be comprised of multiple sub-components, as further illustrated in FIG. 4. The various subcomponents may be physically attached to printed circuit board 200, such as by soldering or other suitable electrical couplings. Various components and sub-components of FIG. 2 may interoperate or otherwise communicate by generating signals that are transmitted between the components and sub-components.

Figure 4:
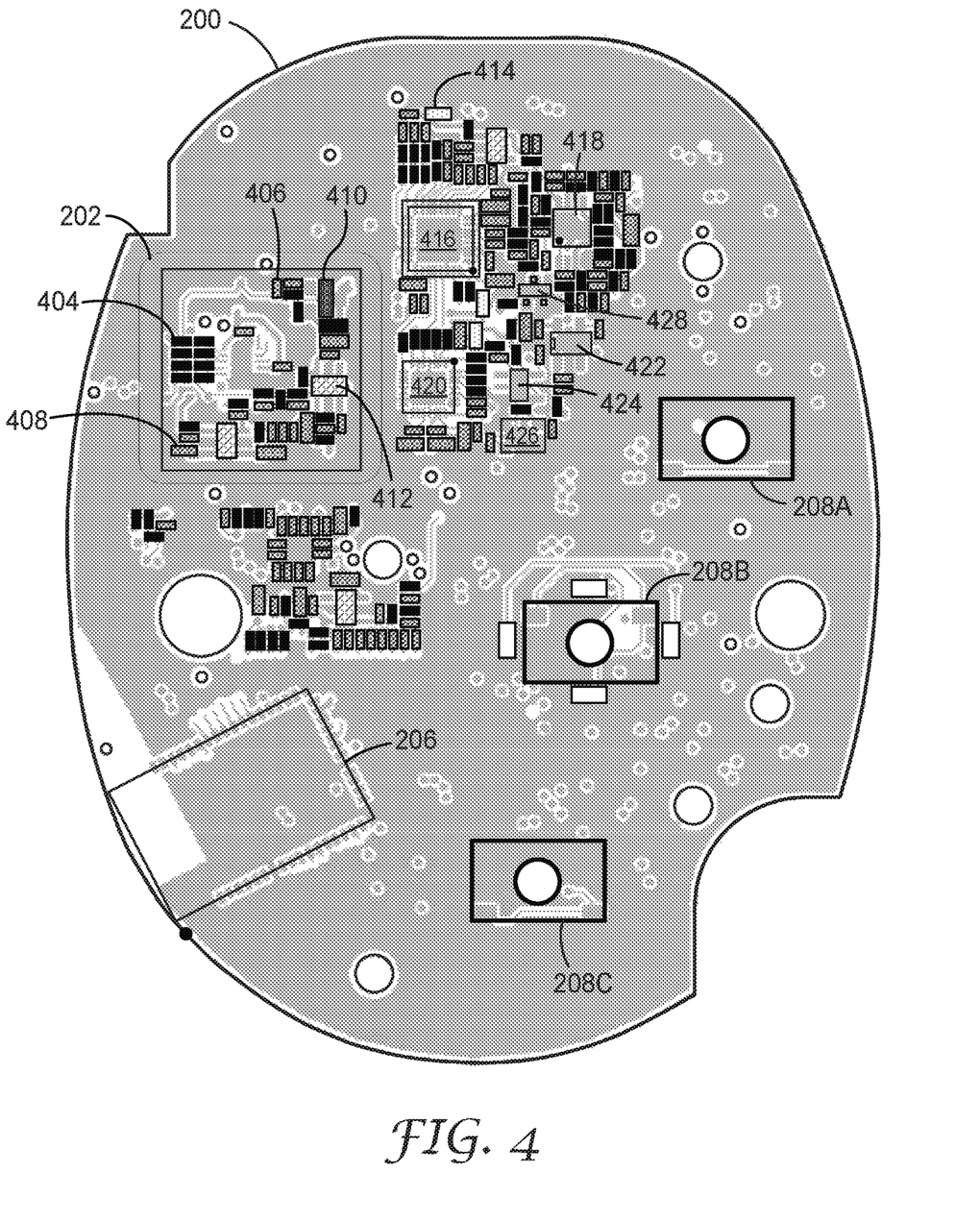
FIG. 4 illustrates sub-components of the various components on the first side of a printed circuit board, in accordance with one or more techniques of the disclosure.

FIG. 4 illustrates sub-components of the various components on the first side of printed circuit board 200, in accordance with one or more techniques of the disclosure. As an example, FIG. 4 illustrates analog radio component 202 with its various sub-components. For instance, analog radio component 202 includes multiple resistors, such as resistor 404. Other like-pictured components of FIG. 4 similar in appearance and size to resistor 404 may also represent resistors with properties that are the same as resistor 404. In some examples, resistor 404 may be a standard-tolerance resistor with 4-digit 0402 code and 0 R decimal position. In some examples, resistor 404 may have a precision or tolerance of 5%.

Analog radio component 406 may also include one or more capacitors, such as capacitor 406. Capacitor 406 may be a standard-tolerance capacitor with a 4-digit code of 0402, and specifications such as X7R, 1 nF, 10%, 50V. Other like-pictured components of FIG. 4 similar in appearance and size to capacitor 406 may also represent capacitors with properties that are the same as capacitor 406. Capacitor 408 may be larger with different specifications than capacitor 406. For instance capacitor 408 may be a standard-tolerance capacitor with 4-digit code of 0603,X7R, 10 uF, 10%, 6.3V. More generally, the size of the capacitor in FIG. 4 may be proportional to the capacitance of the capacitor.

Analog radio component 406 may also include a P-Channel 12-V (D-S) MOSFET 410. Other like-pictured components of FIG. 4 similar in appearance and size to MOSFET 410 may also represent MOSFETS with properties that are the same or similar to MOSFET 410. Analog radio component 412 may also include a linear regulator 412. Other like-pictured components of FIG. 4 similar in appearance and size to linear regulator 412 may also represent linear regulators with properties that are the same or similar to linear regulator 412. In some examples, the linear regulator 412 may include specifications, such as 300 mA, CMOS Linear regulator, 0.8~3.0V (adjustable), TSOT-5. Analog radio component 406 may include a ferrite chip bead 414. Other like-pictured components of FIG. 4 similar in appearance and size to ferrite chip bead 414 may also represent ferrite chip beads with properties that are the same or similar to ferrite chip bead 414. In some examples, the ferrite chip bead 414 may include specifications, such as 4-digit code 0603, 30 ohm, 1 A. Codec 414 may be a component that decodes and encodes audio signals and/or data. Examples of codec 414 may include specifications such as IC Audio Codec 24 bit, 96 Khz, LFCSP-32. Printed circuit board 200 may include operational amplifier 418. Operational amplifier 418 may include specifications, such as being Rail-to-Rail Output Operational Amplifier, 40~+85° C., MSOP8.

Printed circuit board 200 may include an audio ADC (analog to digital converter) 420. Audio ADC 420 may include specifications, such as being a Low Power Stereo Audio ADC, QFN-28. Examples of audio ADC 420 may include but are not limited to Everest ES8288 ADC. Printed circuit board 200 may include a dropout regulator 422. Dropout regulator 422 may include specifications, such as being an IC LDO Regulator SOT-23. Printed circuit board 200 may include an invert 424. Inverter 242 may have a voltage range of 2.0 V to 6.0 V. Printed circuit board 200 may include a resonator 426. Resonator 426 may be a crystal quartz resonator with specifications including 12,000 MHz, SMD3225, 10 ppm. Printed circuit board 200 also illustrates switches 208A-208C. Wireless component 206, in FIG. 4 may be a Bluetooth module, with specifications such as Bluetooth certified 4.0 Audio module. Printed circuit board 200 may include transistor 428. Transistor 428 may include specifications, such as NPN 500 MA, 45V, SOT323.

FIG. 5 illustrates sub-components of the various components on a second, opposite side of printed circuit board 200, in accordance with one or more techniques of the disclosure. In some examples, the second side printed circuit board 200 may be opposed to the first side. As shown in FIG. 5, printed circuit board 200 includes speech and sidetone component 502, analog radio component 506, digital radio component 504, and microprocessor and memory 508 (or "microprocessor 508). Each of the components shown in FIG. 5 may be comprised of one or more sub-components as further illustrated in FIG. 7. Printed circuit board 200 may include a microphone connector 510 that connects to microphone 114 to capture audio of the environment that includes headset 100.

Analog radio component 506 may receive analog audio signals from analog radio component 202, where analog radio component 202 received the audio signals from one or more remote computing devices. Analog radio component 506 may convert the received audio signal into an output audio signal that is sent, via SASMC 204 to one or more of speakers 112. That is, the analog audio signal received by analog radio component 202 may not be directly sent to speakers 112 but instead first transformed by analog radio component 506 for output at speakers 112. Analog radio component 506 may receive audio signals from microphone 114 and convert the audio signals into a form that is wirelessly transmissible (e.g., analog-transmissible audio signal) to another computing device. Analog radio component 506 may send the analog-transmissible audio signal to analog radio component 202, which in turn may send the transmissible signal to one or more other computing devices on a selected frequency.

Digital radio component 504 converts a digital information encoded in an analog signal from analog radio component 202 and converts the signal to an output audio signal that speakers 112 may output. For instance, digital radio component 504 may receive a digital sound signal that digital radio component 504 converts to an output audio signal and sends to SASMC 204. SASMC 204 may cause speakers 112 to output sound corresponding to the output audio signal. Digital radio component 504 may receive audio signals from microphone 114 and convert the audio signals into a form that is wireless transmissible to another computing device. Digital radio component 504 may send the wirelessly transmissible signal to analog radio component 202, which in turn may send the transmissible signal to one or more other computing devices on a selected frequency.

Printed circuit board 200 may include speech microphone and sidetone component 502 ("SMSC 502"). SMSC 502 may receive audio signals from microphone 114 and determine whether the volume of the audio satisfies a threshold (e.g., is greater than a threshold). If the audio signal satisfies a threshold, SMSC 502 may send a signal to microprocessor 508, which in turn causes SASMC 204 to output the signal as sound at one or more of speakers 112. SMSC 502 may send the signal to one or more of digital radio component 504 and/or analog radio component 506, and one or more of these receiving components may wireless transmit a corresponding signal to one or more other computing devices.

Microprocessor 508 may represent any microprocessor and/or memory communicatively coupled to microprocessor 508. Microprocessor 508 may process instructions specified by an instruction set architecture. Microprocessor 508 may perform a variety of functions including but not limited to: implementing functionality of state diagrams in FIGS. 9-11, encoding and/or decoding digital speech signals, implementing voice activated control and user interfaces described in this disclosure, implementing settings of headset 100, and performing frequency selection based on user input.

Figure 6:
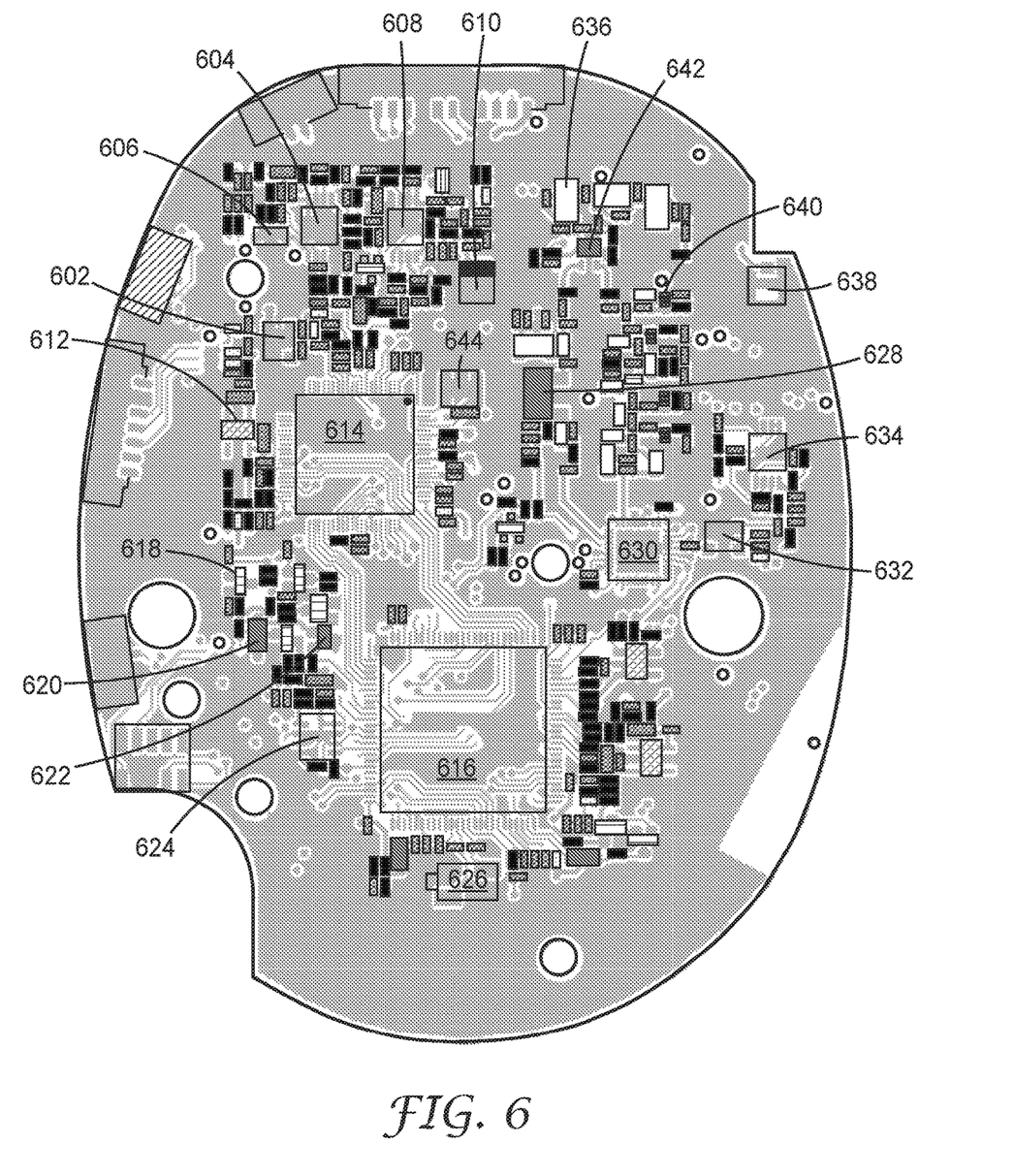
FIG. 6 illustrates sub-components of the various components on the second side of a printed circuit board, in accordance with one or more techniques of the disclosure.

FIG. 6 illustrates sub-components of the various components on the second side of printed circuit board 200, in accordance with one or more techniques of the disclosure. Like-pictured resistor and capacitor components of FIG. 4 also correspond to resistor and capacitor components in FIG. 6. Printed circuit board 200 may include an oscillator 602 with specifications such as 12.288 MHz, 3.3V±20 ppm (+40° C./+85° C.). Printed circuit board 200 may include Rail-to-Rail Output Operational Amplifiers, 40~+85° C., MSOP8. Printed circuit board 200 may include specifications such as Diode Low Volt High Speed Switching, SC-70-2 leads. Printed circuit board 200 may include Rail-to-Rail Output Operational Amplifiers, 40~+85° C., MSOP8. Printed circuit board 200 may include Tant Cap 610 with specifications such as General, Size A, 22 uF, 20%, 6.3V. Printed circuit board 200 may include linear regulator 612. Printed circuit board 200 may include digital radio 614. Printed circuit board 200 may include a microprocessor 616 with specifications, such as MCU ARM M4 32 b 1 MB flash 100-LQFP. Printed circuit board 200 may include transistors, such as transistor 610, which may have specifications such as PNP resistor-equipped transistor; R1=10 kohm, R2=10 kohm. Printed circuit board 200 may include a diode, such as diode 620 with specifications such as Diode Low Volt High Speed Switching, SC-70-2 leads. Other diodes may include diode 622 with specifications such as Schottky barrier(double) diode 30V, SOT323. Printed circuit board 200 may include memory, such as multiple I/O Serial flash memory features 4 KB sector erase. Printed circuit board 200 may include oscillator 626 with specifications, such as CRYSTAL 8.000 MHZ 8 PF SMD. Printed circuit board 200 may include a MOSFET 628, which have specifications such as N-ch Mosfet.UPAK.

Printed circuit board 200 may include an analog radio 630 for wireless analog radio transmissions. Printed circuit board 200 may include an oscillator 632 having specifications, such as Storage Temperature 40~+85° C., ±2.5 PPm, 26 MHz, Size: 3.2×2.5×0.9 mm. Printed circuit board 200 may include operational amplifier 634 with specifications such as Rail-to-Rail Output Operational Amplifier, 40~+85° C., MSOP8. Printed circuit board 636 may include one or more air coils, such as air coil 636. Air coil 636 may have specifications, such as Air Coil SMD 1008, 15 nH, 10%. Other like-pictured components may also be air coils in FIG. 6. The size of the air coil may correspond to the inductance range of the coil. Antenna connector 638 may be included on printed circuit board 200, which couples to antenna 107. Printed circuit board 200 may include diodes, such as diode 640. Diode 640 may include specifications, such as Diode VCO for UHF Band Radio, SMD-2 leads. Printed circuit board 200 may include a switch 642, having specifications such as 20 MHz-2.5 GHz GaAs SPDT switch 6 pin SC-70. Printed circuit board 644 may include a power inductor 644. Power inductor 644 may include specifications such as 47 uH, 20%, size: 3.0×1.2 mm. As described above, like-pictured components of FIG. 6 may have similar or the same properties as the described components above. In some examples, the size of the component as pictured in FIG. 6 may correspond to one or more of its properties. For example purposes, various components have been described with particular specifications in FIGS. 4 and 6; however, one of skill in the art will appreciate that other alternative combinations of alternative components are possible within the spirit and scope of this disclosure.

Figure 7:
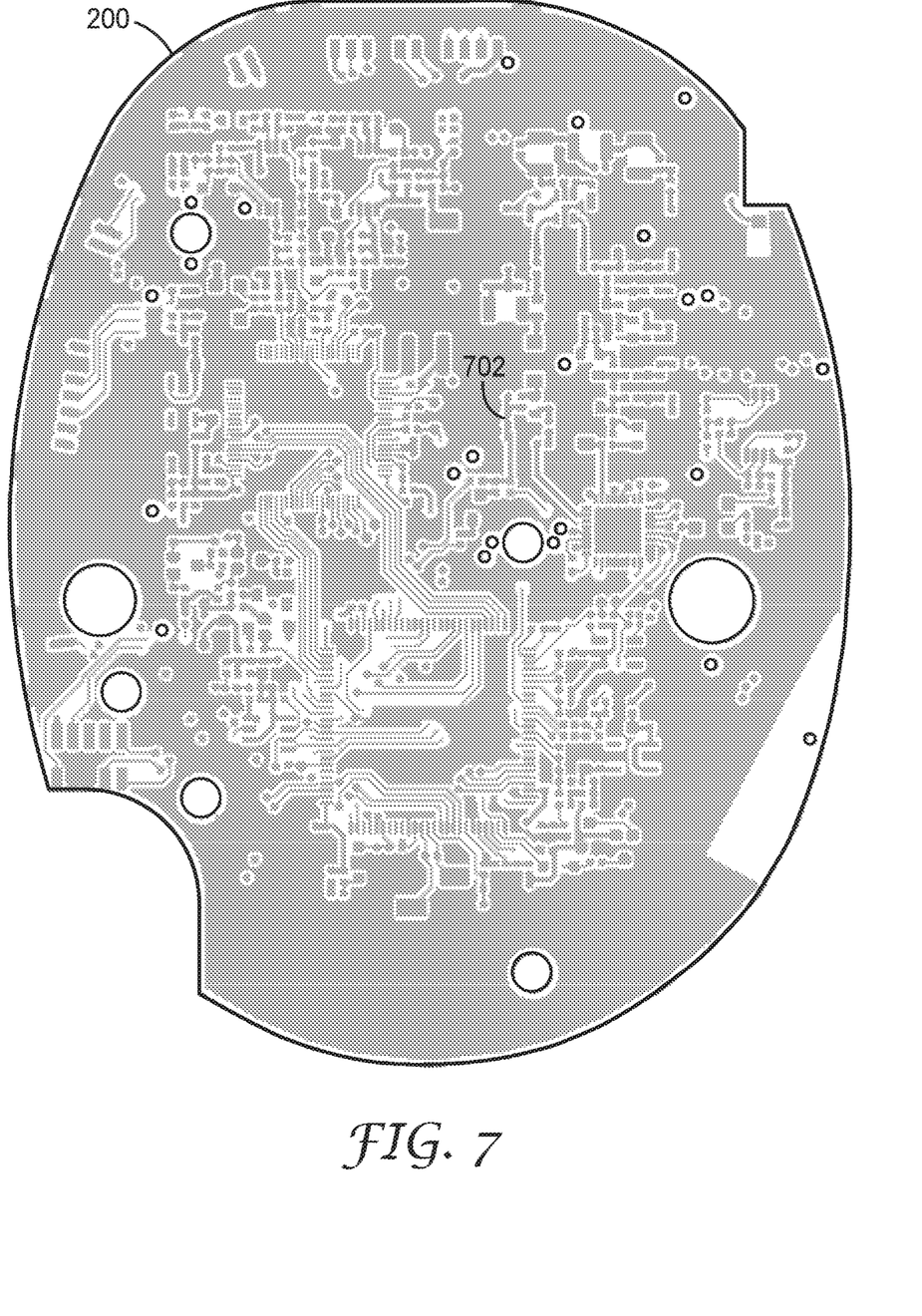
FIG. 7 illustrates traces of the second side of a printed circuit board, in accordance with one or more techniques of the disclosure.

FIG. 7 illustrates traces of the second side of printed circuit board 200, in accordance with one or more techniques of the disclosure. Example trace 702 may provide an electrically communicative coupling between one or more components or sub-components attached to printed circuit board 200. Traces may be electrically conducting thereby enabling the transmission of electrical signals between components and sub-components. The various components on circuit board 200, illustrated in FIG. 6, may be attached to printed circuit board 200. The various components of circuit board 200 as illustrated in FIG. 5, may be comprised of multiple sub-components, as further illustrated in FIG. 6. The various subcomponents may be physically attached to printed circuit board 200, such as by soldering or other suitable electrical couplings. Various components and sub-components of FIG. 4 may interoperate or otherwise communicate by generating signals that are transmitted between the components and sub-components.

Figure 8:
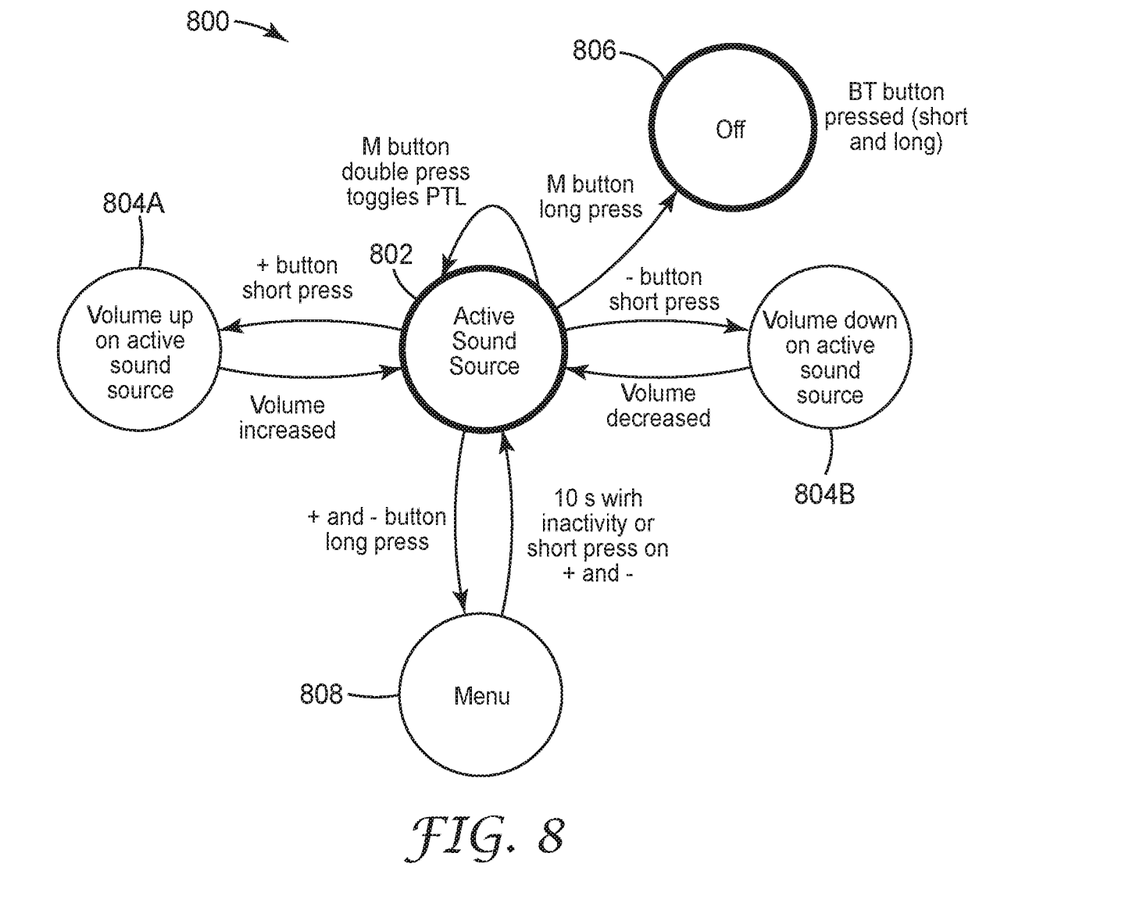
FIG. 8 illustrates a state diagram for a user interface implemented by a microprocessor of a headset, in accordance with techniques of this disclosure.

FIG. 8 illustrates a state diagram 800 for a user interface implemented by microprocessor 508 of headset 100, in accordance with techniques of this disclosure. In some examples, the user interface for headset 100 may be an audio interface that receives spoken words or sounds at microphone 114 and/or touch inputs at switches of headset 100 as inputs. The user interface for headset 100 may be an audio interface that outputs tones, sounds or words as output through speakers 112. In some examples, state diagram 800 may be implement as a state machine in a combination of hardware and/or software. If headset 100 is in an active sound source state 802, headset 100 may be outputting sound via speakers 112. The sound may be from a computing device communicatively coupled via wireless component 206 or the sound may be from another computing device that was received via a wireless transmission using audio radio component 202.

If headset 100 is in active sound state 802, and a user actuates switch 208A to increase the volume or actuates switch 208C to decrease the volume, microprocessor 508 may receive a signal from the respective switch and enter state 804A or 804B. In state 804A or 804B, microprocessor 508 may send a signal to SASMC 204 to increase or decrease the volume of speakers 112 because on the signal received from the respective switch. Upon altering the volume, microprocessor 508 may return to active sound source state 802. In some examples, if headset 100 is in active sound source state 802 and an input is received at switch 208B, which includes pressing switch 208B for longer than a threshold period of time, then microprocessor 508 enter state 806 which may cause headset 100 to power off. If headset 100 is in active sound source state 802 and the switches 208A and 208C are pressed simultaneously or substantially simultaneously (e.g., within a threshold time period of one another), then microprocessor 508 will transition to menu state 808. Operations and states of menu state 808 are further described in FIG. 9.

Figure 9:
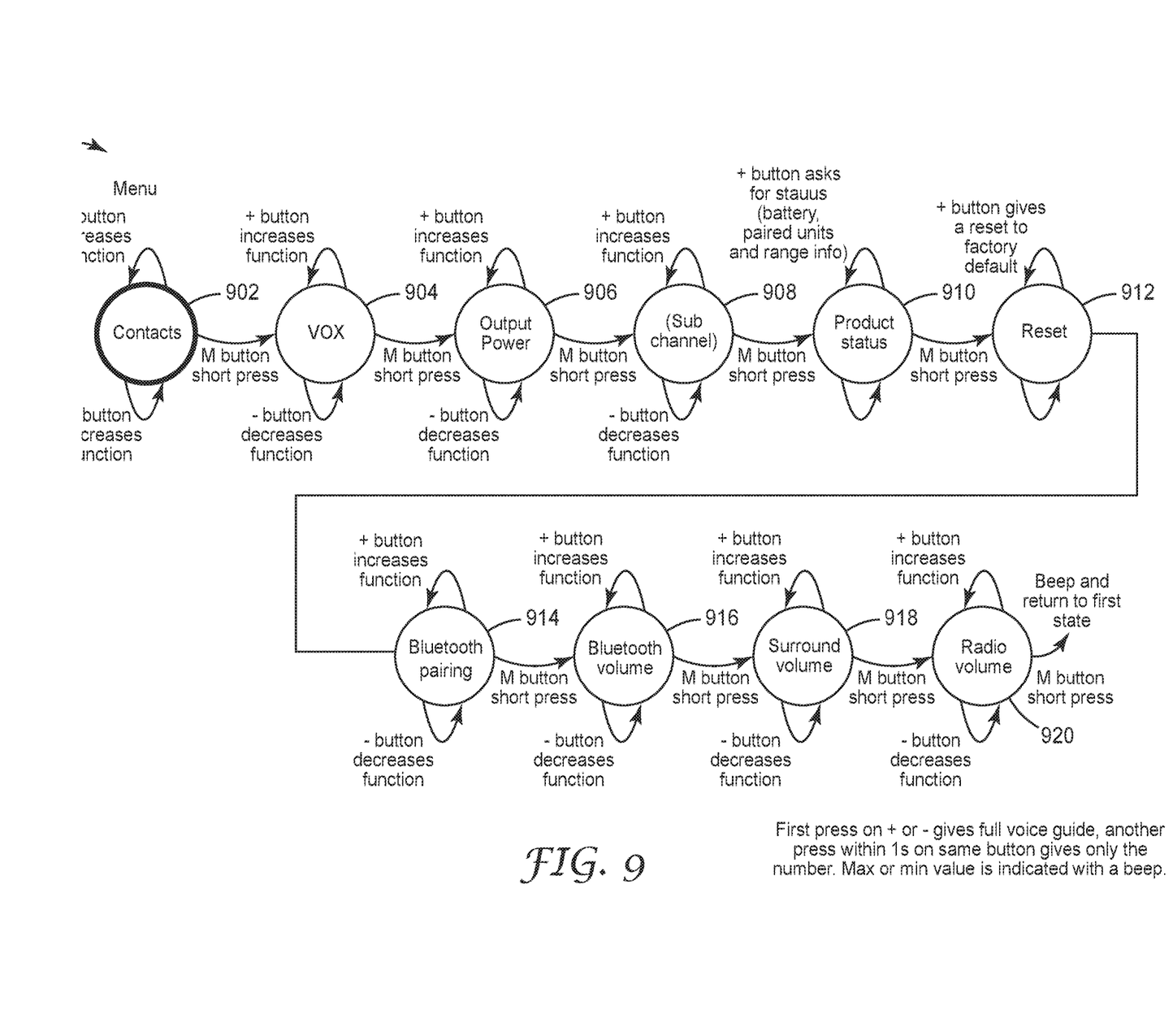
FIG. 9 illustrates a state diagram with comprising states of a menu state, in accordance with techniques of this disclosure.

FIG. 9 illustrates a state diagram 900 with comprising states of menu state 808, in accordance with techniques of this disclosure. Upon entering menu state 808, microprocessor 508 may be in contacts state 902. In contacts state 902, a user may iterate through and select a contact from set of contacts (e.g., address book entries) in a computing device that is wireless coupled to headset 100 via wireless component 206. If microprocessor 508 determines that switch 208A has been actuated, microprocessor 508 may advance from a currently selected contact to a next contact. If microprocessor 508 determines that switch 208C has been actuated, microprocessor may advance from a currently selected contact to a previous contact. In such examples, each of the contacts (having respective contact information stored as structured data including but not limited to name, channel frequency, phone number), may be stored in a list which may be traversed in a sequential manner. When a new contact is selected, headset 100 may cause the name, channel frequency, phone number to be output as sound in speakers 112. In some examples, if the user of headset 100 wishes to select the current contact to call or otherwise communicate with the contact, the user may provide an input that microprocessor 508 may use to initiate the call or communication with the contact.

If microprocessor 508 determines that switch 208B has been actuated while in contact states 902, microprocessor 508 may transition to VOX (or voice-activated) state 904. VOX state 904 may enable a user to increase or decrease a voice-activation threshold. If SMASC 502 determines that a user's voice satisfies (e.g., is greater than or equal to) the voice-activation threshold, then headset 100 may wirelessly transmit sound from microphone 114 to another computing device using analog radio component 202. If microprocessor 508 determines that switch 208A has been actuated while in VOX state 904, then microprocessor 508 may increase the voice-activation threshold, and if microprocessor 508 determines that switch 208C has been actuated while in VOX state 904, then microprocessor 508 may decrease the voice-activation threshold. If microprocessor 508 determines that switch 208B has been actuated, then microprocessor 508 may advance to output power state 906.

In output power state 906, a user may increase or decrease the output power or amplification of a signal transmitted by analog radio component 202. For instance, headset 100 may enable the transmission of a wireless signal representing audio at different power levels. Higher power levels may amplify a signal more than lower power levels. If microprocessor 508 determines that switch 208A has been actuated while in output power state 906, then microprocessor 508 may increase the output power level, and if microprocessor 508 determines that switch 208C has been actuated while in output power state 906, then microprocessor 508 may decrease the output power level. If microprocessor 508 determines that switch 208B has been actuated, then microprocessor 508 may advance to sub-channel state 908.

In sub-channel state 908, a user may select a sub-channel within a frequency for sending and receiving wireless signals. In some examples, multiple sub-channels may exist within a particular frequency. By encoding a sub-channel identifier within a signal, headset 100 may transmit wireless signals on a particular sub-channel. If microprocessor 508 determines that switch 208A has been actuated while in sub-channel state 908, then microprocessor 508 may increase the sub-channel identifier (e.g., if sub-channels are integers or rational numbers), and if microprocessor 508 determines that switch 208C has been actuated while in sub-channel state 908, then microprocessor 508 may decrease the sub-channel. If microprocessor 508 determines that switch 208B has been actuated, then microprocessor 508 may advance to product status state 910.

In product-status state 910, headset 100 may provide audio output via speakers 112 that indicates the product status information of headset 100. Product status information may include remaining battery life, frequency, sub-channel, other computing devices that are paired with headset 100, and range information of other computing devices or headsets. Product information may include any information that is descriptive of headset 100 or other devices communicatively coupled or which may be coupled to headset 100. If microprocessor 508 determines that switch 208A has been actuated while in product status state 910, then headset 100 may output various product information. If microprocessor 508 determines that switch 208B has been actuated, then microprocessor 508 may advance to reset state 912. In reset state 912, if microprocessor 508 determines that switch 208A has been actuated, then microprocessor 508 may perform a factory reset of headset 100 which resets headset 100 to a set of initial settings that are configured before a first use of the headset 100 by a user who has purchased headset 100. If microprocessor 508 determines that switch 208B has been actuated, then microprocessor 508 may advance to Bluetooth pairing state 914.

In Bluetooth pairing state 914 a user may cause headset 100 to search in a pairing mode for another computing device within range of headset 100 to which headset 100 may establish a connection. In a pairing mode, headset 100 and another computing device may exchange information to establish the connection. Although described in the context of Bluetooth protocol, any suitable wireless protocol may be used. If microprocessor 508 determines that switch 208A has been actuated while in Bluetooth pairing state 914, then microprocessor 508 may place headset 100 in the pairing mode, and if microprocessor 508 determines that switch 208C has been actuated while in Bluetooth pairing state 914, then microprocessor 508 may exit the pairing mode. If microprocessor 508 determines that switch 208B has been actuated, then microprocessor 508 may advance to Bluetooth volume state 916.

In Bluetooth volume state 916, a user may select a volume level of audio data output by speakers 112 and received from another computing device that is coupled to headset 100 using wireless component 206. Although described in the context of Bluetooth protocol, any suitable wireless protocol may be used. If microprocessor 508 determines that switch 208A has been actuated while in Bluetooth volume state 916, then microprocessor 508 may increase the volume level, and if microprocessor 508 determines that switch 208C has been actuated while in Bluetooth volume state 916, then microprocessor 508 may decrease the volume level. If microprocessor 508 determines that switch 208B has been actuated, then microprocessor 508 may advance to surround volume state 918.

In surround volume state 918, a user may select a volume level of situational awareness function, which may input sound from the environment which headset 100 is used into headset 100. If microprocessor 508 determines that switch 208A has been actuated while in surround volume state 918, then microprocessor 508 may increase the situational awareness volume level, and if microprocessor 508 determines that switch 208C has been actuated while surround volume state 918, then microprocessor 508 may decrease the situational awareness volume level. If microprocessor 508 determines that switch 208B has been actuated, then microprocessor 508 may advance to radio volume state 920.

In radio volume state 920, a user may select a volume level of audio received via wireless transmission using analog radio component 202. If microprocessor 508 determines that switch 208A has been actuated while in radio volume state 920, then microprocessor 508 may increase the volume level, and if microprocessor 508 determines that switch 208C has been actuated while radio volume state 920, then microprocessor 508 may decrease the volume level of audio received via wireless transmission using analog radio component 202. If microprocessor 508 determines that switch 208B has been actuated, then microprocessor 508 may advance to contacts state 902.

Figure 10:
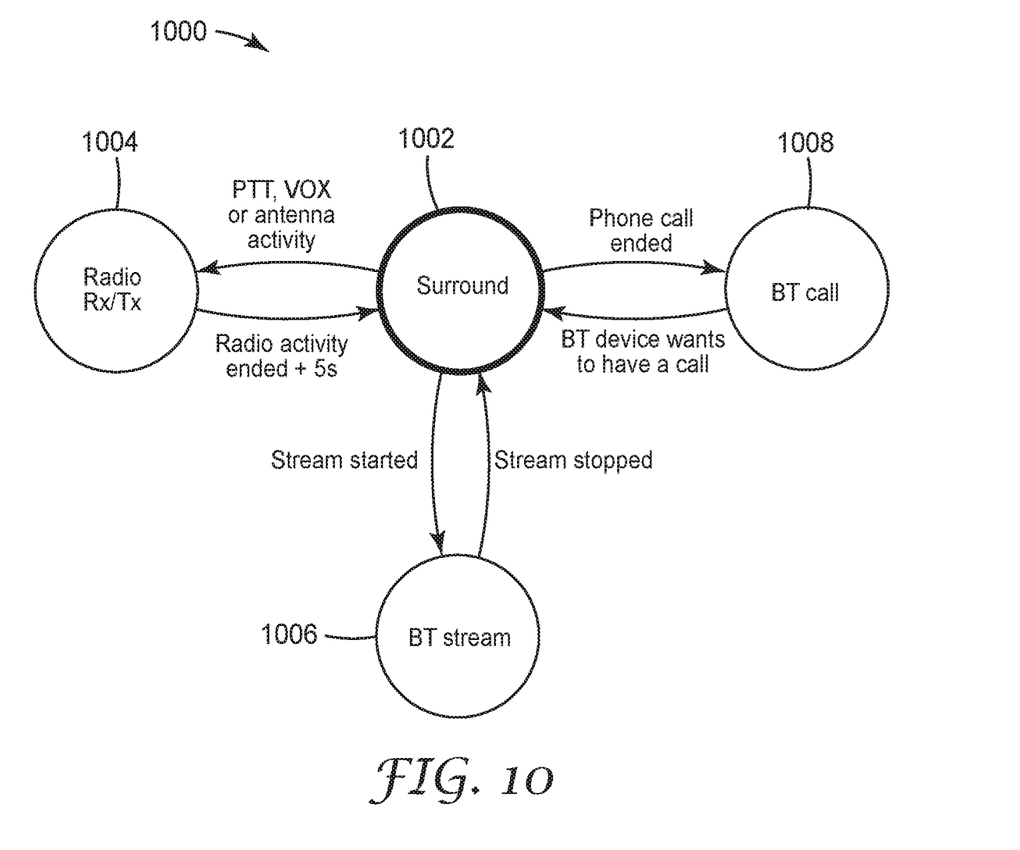
FIG. 10 illustrates a state diagram for transitioning between sound sources, in accordance with techniques of this disclosure.

FIG. 10 illustrates a state diagram 1000 for transitioning between sound sources, in accordance with techniques of this disclosure. In surround state 1002, headset 100 may output, in speakers 112, ambient sound from the environment that includes headset 100. If microprocessor 508 detects sound from microphone 114, an incoming wireless transmission from analog radio component 202, or a user input (e.g., selection of a switch) for Push-To-Talk (e.g., while push-to-talk is activated, microphone 114 is activated and captures audio which may be transmitted), microprocessor 508 may transition to radio transmission state 1004. In radio transmission state 1004, microprocessor 508 may send and/or receive audio signals that are received at microphone 114 and/or analog radio component 202. In radio transmission state 1004, headset 100 may transmit audio signals captured via microphone 114 via analog radio component 202 to other computing devices. In radio transmission state 1004, headset 100 may receive audio signals from other computing devices via analog radio component 202 and output sound at speakers 112 that corresponds to the audio signals. If analog radio component 202 has not sent or received an audio signal for a threshold period of time or more, then microprocessor 508 may transition from radio transmission state 1004 to surround state 1002.

If a user selects a wireless source, such as a Bluetooth connected computing device to input audio into headset 100, microprocessor 508 may transition to Bluetooth stream state 1006. In Bluetooth stream state 1006 microprocessor 508 may cause headset 100 to output sound in speakers 112 that corresponds to audio data in a stream received from a computing device that is wirelessly coupled to headset 100 via wireless component 206. If microprocessor 508 determines that the stream has terminated, microprocessor 508 may transition to surround state 1002. If microprocessor 508 receives a signal of an incoming call, such as a Bluetooth call from a computing device that is communicatively coupled to headset 100, then microprocessor 508 may transition to Bluetooth call state 1008. In Bluetooth call state 1008, headset 100 may receive call data corresponding to a call that is received at a computing device communicatively coupled to headset 100 via wireless component 206. Microprocessor 508 may cause speakers 112 to output sound at speakers 112 that corresponds to the audio data. Upon determining that the call has ended, microprocessor 508 may transition to surround state 1002.

In some examples, headset 100 may have a particular classification. For instance, headset 100 may have a highest classification for Intrinsically Safe use (for use on oil rigs, open and closed mines). Intrinsically safe versions of headset 100 may be approved for use in mines (both open and closed) and for use on oil rigs. In some examples, an intrinsically safe version may have the highest possible classification for a hearing protector. An intrinsically safe version may be constructed by changing plastic material in cups and changing headband material to materials that are approved for use in mines and/or oil rigs. An intrinsically safe version of headset 100 may include a particularly approved Lithium Ion battery that satisfies one or more requirements to be intrinsically safe. Such requirements may include battery composition or construction, battery environmental specifications, or any other specification of a battery. In some examples, a power source, such as a battery may be coupled to one or more printed circuit boards in headset 100 to power the electrical components.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor", as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the embodiment, certain acts or events of any of the methods described herein can be performed in a different sequence, may be added, merged, or left out all together (e.g., not all described acts or events are necessary for the practice of the method). Moreover, in certain embodiments, acts or events may be performed concurrently, e.g., through multi-threaded processing, interrupt processing, or multiple processors, rather than sequentially.

In some examples, a computer-readable storage medium includes a non-transitory medium. The term "non-transitory" indicates, in some examples, that the storage medium is not embodied in a carrier wave or a propagated signal. In certain examples, a non-transitory storage medium stores data that can, over time, change (e.g., in RAM or cache).

Various examples have been described. These and other examples are within the scope of the following claims.

What is claimed is:

1. An acoustic headset for providing hearing protection, comprising:
   a first auditory cup having one or more integrated speakers;
   a second auditory cup having one or more integrated speakers;
   at least one of a stirrup or headband interconnecting the first and second auditory cups;
   a microphone that receives sound, wherein the microphone is coupled to the acoustic headset; and
   wherein at least one of the auditory cups comprises a digital component for transmission and receipt of digital wireless audio communications, and wherein at least one of the auditory cups comprises an analog component for transmission and receipt of analog wireless audio communications, wherein the acoustic headset is configured to output first audio at the auditory cup integrated speakers based on an incoming digital wireless audio communication received by the digital component, wherein responsive to the analog component receiving an incoming analog wireless audio communication, the acoustic headset is further configured to interrupt the first audio in a selected one of the auditory cup integrated speakers, and to output second audio at the selected speaker based on the incoming analog wireless audio communication while continuing to output first audio at the non-selected auditory cup integrated speakers.

2. The acoustic headset of claim 1, wherein the digital component and the analog component are included on a printed circuit board, and wherein the printed circuit board is included within the first auditory cup.

3. The acoustic headset of claim 2, wherein the printed circuit board has dimensions within a range of 4.5 cm width by 6.3 cm height to 8.5 cm width by 10.3 cm height.

4. The acoustic headset of claim 2, wherein a surface area of the printed circuit board less than 55 square centimeters.

5. The acoustic headset of claim 4, wherein the printed circuit board having the surface area of less than 55 square centimeters is included in the first auditory cup having a cavity with a cubic volume of less than 425 cubic centimeters.

6. The acoustic headset of claim 2, wherein the printed circuit board includes a microprocessor.

7. The acoustic headset of claim 6, wherein the microprocessor is included on a side of the printed circuit board that includes the digital component and the analog component.

8. The acoustic headset of claim 6, wherein the microprocessor provides a user interface to change one or more settings associated with the acoustic headset, and wherein the microprocessor changes the one or more settings based at least in part on user input from one or more switches integrated in the acoustic headset or based at least in part on one or more audio inputs received from the microphone.

9. The acoustic headset of claim 8, wherein the microprocessor implements a state machine comprising a plurality of states that represent the user interface.

10. The acoustic headset of claim 1, wherein the digital component and the analog component are included on a first side of the printed circuit board.

11. The acoustic headset of claim 10, wherein the analog component is a first analog component that converts an audio signal from the microphone to an analog transmissible audio signal, and wherein one of the first or second auditory cups comprises a second analog component for transmission of the analog transmissible audio signal on a particular frequency.

12. The acoustic headset of claim 11, wherein the second analog component for transmission of the analog transmissible audio signal is included on a second side of the printed circuit board that is opposite to the first side of the printed circuit board.

13. The acoustic headset of claim 11, wherein the second analog component for transmission of the analog transmissible audio signal is included on a second printed circuit board, wherein the first printed circuit board is included in the first auditory cup and the second printed circuit board is included in the second auditory cup, and wherein the first printed circuit board is communicatively coupled to the second printed circuit board by a communication link.

14. The acoustic headset of claim 1, wherein the digital component is included on a first printed circuit board and wherein the first printed circuit board is included within the first auditory cup, wherein the analog component is included on a second printed circuit board and wherein the second printed circuit board is included within the second auditory cup, and wherein the first printed circuit board is communicatively coupled to a second printed circuit board by a communication link.

15. The acoustic headset of claim 1, wherein no additional components external to the acoustic headset are used to assist the digital component for the transmission and receipt of the digital wireless audio communications.

16. The acoustic headset of claim 1, wherein no additional components external to the acoustic headset are used to assist the analog component for the transmission and receipt of the analog wireless audio communications.

17. The acoustic headset of claim 1, wherein the acoustic headset is a first acoustic headset, wherein transmission and receipt of the digital wireless audio communications or transmission and receipt of the analog wireless audio communications are with a second acoustic headset.

18. The acoustic headset of claim 1, wherein at least one of the first or second audio cups has dimensions in a range of 2.9 cm depth by 8.8 cm height by 6.3 cm width to 8.9 cm depth by 14.8 cm height by 12.3 cm width.

* * * * *